United States Patent
Yin et al.

(10) Patent No.: US 9,927,304 B2
(45) Date of Patent: Mar. 27, 2018

(54) APPARATUS AND METHOD FOR DETERMINING CORE TEMPERATURE OF FOOD

(71) Applicant: KONINKLIJKE PHILIPS N.V., Eindhoven (NL)

(72) Inventors: Bin Yin, Eindhoven (NL); Ling Ling Cao, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 329 days.

(21) Appl. No.: 14/655,376

(22) PCT Filed: Dec. 27, 2013

(86) PCT No.: PCT/IB2013/061372
§ 371 (c)(1),
(2) Date: Jun. 25, 2015

(87) PCT Pub. No.: WO2014/102746
PCT Pub. Date: Jul. 3, 2014

(65) Prior Publication Data
US 2015/0362378 A1    Dec. 17, 2015

(30) Foreign Application Priority Data

Dec. 27, 2012 (WO) ................ PCT/CN2012/087650

(51) Int. Cl.
*G01K 3/10* (2006.01)
*F24C 7/08* (2006.01)
(Continued)

(52) U.S. Cl.
CPC ................ *G01K 3/10* (2013.01); *F24C 7/087* (2013.01); *F24C 7/088* (2013.01); *G01N 33/02* (2013.01); *H05B 1/0263* (2013.01)

(58) Field of Classification Search
CPC   G01K 7/02; G01K 7/22; G01K 13/02; G01K 2205/04; G01K 2013/024;
(Continued)

(56) References Cited

U.S. PATENT DOCUMENTS

| | | | |
|---|---|---|---|
| 4,401,884 A | 8/1983 | Kusunoki | |
| 6,299,920 B1 * | 10/2001 | Saksena | ................ G01K 11/22 374/149 |

(Continued)

FOREIGN PATENT DOCUMENTS

| | | |
|---|---|---|
| CN | 102119770 A | 7/2011 |
| DE | 102007008894 A1 | 8/2008 |

(Continued)

*Primary Examiner* — Manish S Shah

(57) ABSTRACT

The invention proposes a method of determining core temperature of food in a closed container, the method including the steps of: adjusting heating power supplied to the container to allow internal temperature of the container to change within a predetermined duration; obtaining information related to the change of internal temperature of the container; and determining the core temperature of the food based on the information related to the change of internal temperature and predetermined relationships between information related to change of internal temperature of the container and core temperatures of the food. The invention also proposes an apparatus for determining core temperature of food and a food processing device.

15 Claims, 5 Drawing Sheets

(51) Int. Cl.
*H05B 1/02* (2006.01)
*G01N 33/02* (2006.01)

(58) Field of Classification Search
CPC ........ H01R 4/023; H01R 4/029; H01R 43/28;
B23K 31/02; H02M 1/32; H02M 1/38;
H02M 1/53806; G01N 25/72; G01R
31/2642; G01R 31/048; G01R 31/40;
H01C 7/008; H01C 17/00
See application file for complete search history.

(56) References Cited

U.S. PATENT DOCUMENTS

| | | |
|---|---|---|
| 2006/0049187 A1 | 3/2006 | Jurgens |
| 2009/0229474 A1 | 9/2009 | Hsu |

FOREIGN PATENT DOCUMENTS

| | | |
|---|---|---|
| EP | 0000959 A1 | 3/1979 |
| EP | 1211913 A2 | 6/2002 |
| RU | 2281619 C1 | 8/2006 |
| WO | 0028292 A1 | 5/2000 |

\* cited by examiner

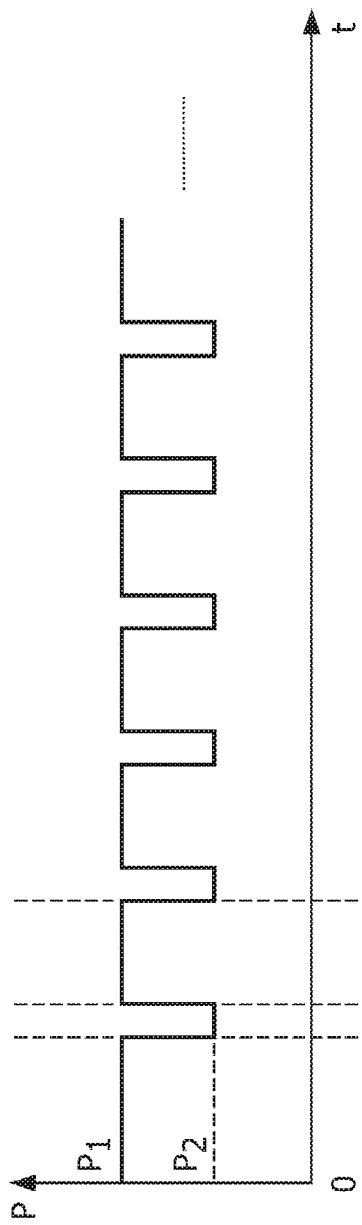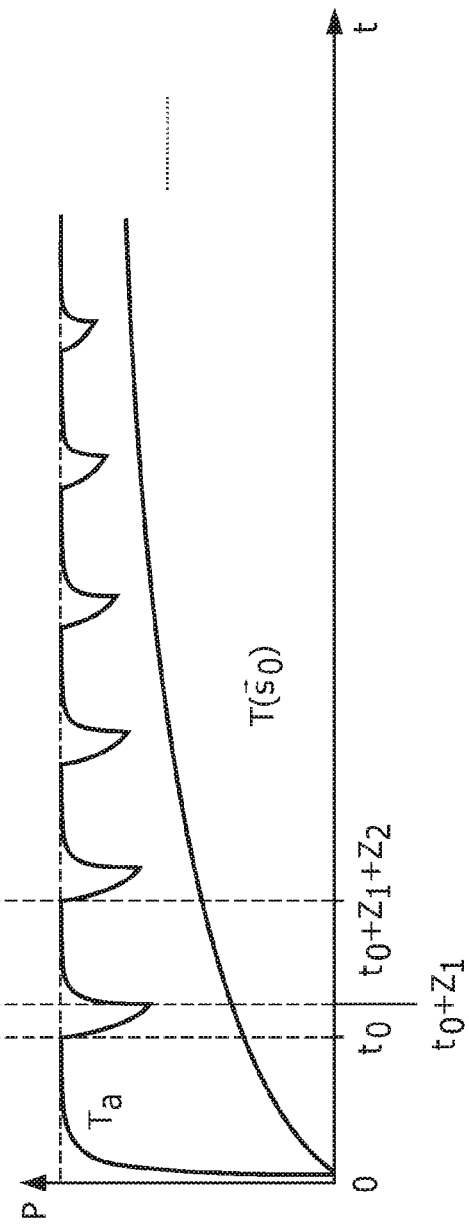

APPARATUS AND METHOD FOR DETERMINING CORE TEMPERATURE OF FOOD

This application is the U.S. National Phase application under 35 U.S.C. §371 of International Application No. PCT/IB2013/061372, filed on Dec. 27, 2013, which claims the benefit of Chinese Application No. PCT/CN2012/087650 filed on Dec. 27, 2012. These applications are hereby incorporated by reference herein.

FIELD OF THE INVENTION

The invention relates to food analysis, and particularly relates to apparatuses and method for determining core temperature of food.

BACKGROUND OF THE INVENTION

Cooking doneness or readiness refers to a status of food being cooked where a good balance of nutrition preservation and taste enhancement is reached. Both undercooking and overcooking give negative consequences in these two aspects, as well as food safety. Food that is undercooked may cause food-borne diseases on its consumers, for the temperature rise and/or its sustaining time are insufficient to kill harmful bacteria or parasites, especially in the inner part of the food. On the other hand, overcooking affects the food taste and texture, for instance due to excessive loss of moisture, and possibly destroys the structure of certain nutrients, which leads to the reduction of their health benefits.

Key to resolve this problem is to monitor core/inner temperature of food during cooking. For detecting core temperature of cooked food, people have been using a needle-shaped thermometer that is punched into the food to provide temperature measure where the needle tip is located. The method is, however, destructive and troublesome, still involving significant amount of manual work.

Other major thermal sensing methods include electromagnetic radiometry (at microwave or infrared range), magnetic resonance thermometry and ultrasound thermometry. These methods are non-destructive and some may sense the temperature a few centimeters deep into the object. However, they either require complex setup thus high cost, or are subject to various disturbing factors thus making the measurement unreliable.

OBJECT AND SUMMARY OF THE INVENTION

In view of the issues stated above, it would be advantageous to achieve a more desirable apparatus and method of determining core temperature of food. It would also be advantageous to achieve a low-cost, easy-to-implement and sufficiently accurate apparatus and method of determining core temperature of food, which is suitable for consumer product applications.

Heat is transferred in various manners such as conduction, convection and radiation. Take the heating process in an oven as an example. First, the heating source is switched on, which heats up the air around it by both radiation and conduction. Meanwhile, the inner wall of the oven, often made of Zinc plates nowadays, gets heated as well by the radiation from the heating source and the heat transferred by the air through convection. The heating of the food is then realized by the radiation, from both the heating source and the warm Zinc plates, and the heat transferred by the air through convection.

Heat flows spontaneously from a system of higher temperature to one of lower temperature. When a food object is placed into a pre-heated oven, the thermal steady state is reinstalled after a short transient period under a control mechanism. At this thermal steady state, the temperature of the surrounding of the food is kept constant since the heat created by the heating sources equals what flows into the food and dissipates elsewhere, which can be expressed as follows.

$$Q_c = Q_h + Q_l \tag{1}$$

where $Q_c$, $Q_h$ and $Q_l$ represent the total heat generated by the heating source, the heat flowing into the food object and the heat lost (e.g., leaking out of the oven), respectively.

At the thermal steady state during heating, the oven temperature (i.e., internal temperature of the oven) $T_a$ stays at a constant temperature, up to a very proximate vicinity of the food surface, from which there exists a negative temperature gradient towards the center of the food. Measuring the internal ambient temperature of the oven, even very close to the food surface, gives a constant readout, thus not being able to reflect the inner temperature/inner temperature variation of the food.

However, as soon as the heating power drops, the heat generated does not suffice to compensate for the heat that is dissipating, and as a result the oven temperature starts to decline. The declination rate depends on the total heat energy that the entire internal oven environment has at the start of the heating power drop, where total heat energy includes that residing in the food and is thus dependent on the volumetric temperature of the food. The oven temperature $T_a$ varies over time as $$T_a(t) = g(T_a(t_0), T(t_0, \vec{s}), Q'_c), t > t_0 \tag{2}$$

where $t_0$ is the time moment when the heating power reduces, $T(t_0, \vec{s})$ represents the temperature spatial distribution of the food at $t_0$, and $Q'_c$ is the heat generated after power lowering (thus $Q'_c < Q_c$). When the food object is to a large extent regular in geometry, e.g., approximately a sphere, a cylinder, a cuboid or an ellipsoid, as well as uniform or well structured (e.g., layered) in terms of its thermal property, equation (2) may reduce to $$T_a(t) = g(T_a(t_0), T(t_0, \vec{s}_0), Q'_c), t > t_0 \tag{3}$$

where $T(t_0, \vec{s}_0)$ is the temperature of the food at its geometrical center (i.e., core temperature) at $t_0$, which means the oven temperature can be unambiguously associated with the core temperature of the food. At a time moment $t_0 + \delta t$, $\delta t$ being a sufficiently short period of time (e.g., a few to a few tens of seconds), the function g( ) may be linearised as $$T_a(t) \approx T_a(t_0) + h(T(t_0, \vec{s}_0)) \times t, t > t_0 \tag{4}$$

where $h(T(t_0, \vec{s}_0))$ gives the temperature drop rate as a function of $T(t_0, \vec{s}_0)$. The analytical form of h is determined mainly by $Q'_c$, thus relating to the heating power when $t > t_0$, as well as the parameters of the food, such as thermal properties and geometry. Given the dimension and type of the food, h may be determined experimentally.

As can be deduced from the above discussion, when the heating power is reduced, the internal temperature of the oven drops. The drop rate of internal temperature of the oven is tightly associated with the core temperature of the food, i.e., the higher the core temperature of the food is, the lower the drop rate of internal temperature of the oven is. Thus, the drop rate of internal temperature of the oven may be used to infer the core temperature of the food.

Based on the above concerns, in one aspect, one embodiment of the invention provides a method of determining core temperature of food in a closed container, the method comprising the steps of: adjusting heating power supplied to the container to allow internal temperature of the container to change within a predetermined duration; obtaining information related to the change of internal temperature of the container; and determining the core temperature of the food based on the information related to the change of internal temperature and predetermined relationships between information related to change of internal temperature of the container and core temperatures of the food.

As the relationships between information related to change of internal temperature of the container and core temperatures of the food is pre-obtained, for example, by experiment, as well as the information related to the change of internal temperature can be easily acquired during cooking without destroying the food, the method of the invention enables an more effective and desirable way of determining the core temperature of the food compared to traditional methods.

In an example, the information related to the change of internal temperature comprises a rate of the change of internal temperature, and the step of obtaining comprises: measuring a plurality of internal temperature values of the container during the predetermined duration at a predetermined distance away from the food in the container; and calculating the rate of the change of internal temperature of the container based on the plurality of internal temperature values.

In another example, the information related to the change of internal temperature comprises an extreme value of the change of internal temperature, and the step of obtaining comprises: measuring the extreme value of the change of internal temperature of the container during the predetermined duration at a predetermined distance away from the food in the container.

In an example, the step of adjusting comprises: decreasing the heating power supplied to the container to allow internal temperature of the container to decrease within the predetermined duration. In this regard, the rate of the change of internal temperature of the container is the drop rate of internal temperature of the container; the extreme value of the change of internal temperature of the container is the extreme value of decrease of internal temperature of the container.

In another example, the step of adjusting comprises: increasing the heating power supplied to the container to allow internal temperature of the container to increase within the predetermined duration. In this case, the rate of the change of internal temperature of the container is the increase rate of internal temperature of the container; the extreme value of the change of internal temperature of the container is the extreme value of increase of internal temperature of the container.

In another aspect, one embodiment of the invention provides a food processing device, comprising: a closed container, configured to receive food; a heater coupled with the container, configured to heat the food in the container; a sensor arranged in the container at a predetermined distance away from the food, configured to measure internal temperature values of the container; and a controller coupled with the heater and the sensor, configured to perform a set of operations of: controlling heating power of the heater to allow internal temperature of the container to change within a predetermined duration; obtaining information related to the change of internal temperature of the container based on at least one internal temperature value that is measured by the sensor during the predetermined duration; and determining the core temperature of the food based on the information related to the change of internal temperature and predetermined relationships between information related to change of internal temperature of the container and core temperatures of the food.

Advantageously, the information related to the change of internal temperature comprises a rate of the change of internal temperature, and the sensor is configured to measure a plurality of internal temperature values of the container during the predetermined duration, and the controller is configured to receive the plurality of internal temperature values from the sensor and calculate the rate of the change of internal temperature of the container based on the plurality of internal temperature.

Advantageously, the information related to the change of internal temperature comprises an extreme value of the change of internal temperature, and the sensor is configured to measure the extreme value of the change of internal temperature during the predetermined duration, and the controller is configured to receive the extreme value of the change of internal temperature from the sensor.

Advantageously, the controller is configured to adjust heating power of the heater to allow internal temperature of the container to change within the predetermined duration.

Advantageously, the controller performs the operations after the food in the container has been cooked for a first predetermined duration.

Advantageously, the controller performs the set of operations periodically.

Advantageously, the frequency of the set of operations performed by the controller increases.

In another aspect, one embodiment of the invention provides an apparatus for determining core temperature of food in a closed container, the apparatus comprising: an adjusting unit configured to adjust heating power supplied to the container to allow internal temperature of the container to change within a predetermined duration; an obtaining unit configured to obtain information related to change of internal temperature of the container; and a determining unit configured to determine the core temperature of the food based on the information related to the change of internal temperature and predetermined relationships between information related to change of internal temperature of the container and core temperatures of the food.

BRIEF DESCRIPTION OF THE DRAWINGS

The above and other objects and features of the present invention will become more apparent from the following detailed description considered in connection with the accompanying drawings, in which:

FIG. 3a shows an example of heating power curve that may be used to obtain predetermined relationships between drop rates of internal temperature of a container and core temperatures of food;

FIG. 3b shows an example of curves of core temperature of the food and internal temperature of the container under the heating power of FIG. 3a;

Throughout the above drawings, like reference numerals will be understood to refer to like, similar or corresponding features or functions.

DETAILED DESCRIPTION

Reference will now be made to embodiments of the invention, one or more examples of which are illustrated in the figures. The embodiments are provided by way of explanation of the invention, and are not meant as a limitation of the invention. For example, features illustrated or described as part of one embodiment may be used with another embodiment to yield still a further embodiment. It is intended that the invention encompass these and other modifications and variations as come within the scope and spirit of the invention.

Figure 1:
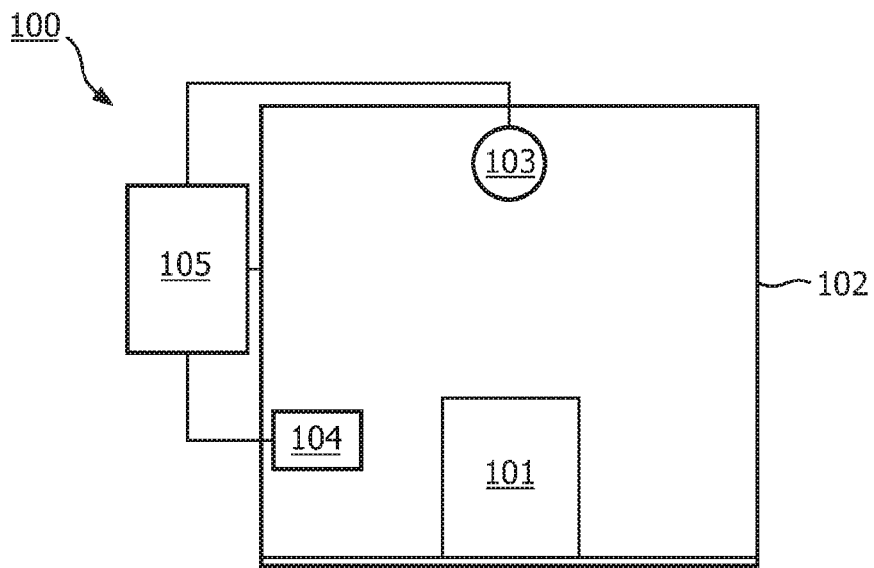
FIG. 1 shows a food processing device according to one embodiment of the invention.

FIG. 1 illustrates a food processing device 100. Food processing device 100 comprises a container 102 for receiving food 101, which may be made of metal, glass or other materials with good thermal conductivity. Advantageously, container 102 may constitute a closed space during the operation of food processing device 100 such that the accuracy of determining the core temperature of food 101 could be improved.

Any suitable types of food are applicable here to have its core temperature to be determined during cooking. Advantageously, foods may be sorted into different categories, each category corresponding to one set of relationships between information related to change of internal temperature of a container and core temperatures of food of this category, which may be obtained in advance by experiment and will be described in details later. In one example, foods may be divided into different categories in terms of its type and size, for instance, the categories may be 'type: fish; size: small', 'type: bread; size: medium', and 'type: chicken; size: big'. In other embodiments, food may be divided into different categories in terms of its type, shape and size.

In other embodiments, each kind of food may correspond to one set of relationships between information related to change of internal temperature of a container and core temperatures of food of this kind. In this case, a lot more sets of relationships are required compared to the situation where foods are sorted into different categories.

Still referring to FIG. 1, food processing device 100 further comprises a heater 103 configured to heat food 101 in container 102. Heater 103 may be disposed in any suitable position where heat generated by heater 103 can be transferred to food 101 by conduction and/or convection and/or radiation, for example, be disposed at the bottom of container 102 and/or at the top of container 102. Various types of heaters may be used herein, for example, a heating tube, a heating plate and so forth.

Food processing device 100 further comprises a sensor 104 configured to measure internal temperature values of container 102. Various kinds of sensors may be used herein to perform such a temperature measurement, for example, a thermocouple sensor, an infrared sensor and so forth. Sensor 104 may be disposed at any suitable position where internal temperature of container 102 can be measured. Advantageously, sensor 104 may be arranged in container 102 at such a predetermined distance away from food 101 that a good balance between the signal-to-noise ratio of sensor 104 and convenience of usage is achieved. For example, the predetermined distance may be in the range of 10 cm to 20 cm.

Food processing device 100 further comprises a controller 105 electrically coupled to heater 103 and sensor 104. Controller 105 may be a micro control unit (MCU), for example. To achieve the purpose of determining the core temperature of food 101, a dynamic heating strategy is adopted, for instance, the heating power of heater 103 is adjusted by controller 105 at some points during the whole cooking process of food 101. To simplify the control procedure of controller 105 and achieve good heating efficiency, advantageously, the adjustments of heating power of heater 103 may occur after food 101 has been cooked for a first predetermined duration, for example, it may occur at a later stage of cooking (i.e., a stage at which the core temperature of food 101 has increased to a certain level), since there is more eager for determining the core temperature of food 101 and thus the doneness of food 101 at the later stage of cooking compared to the earlier stage of cooking.

Figure 2A:
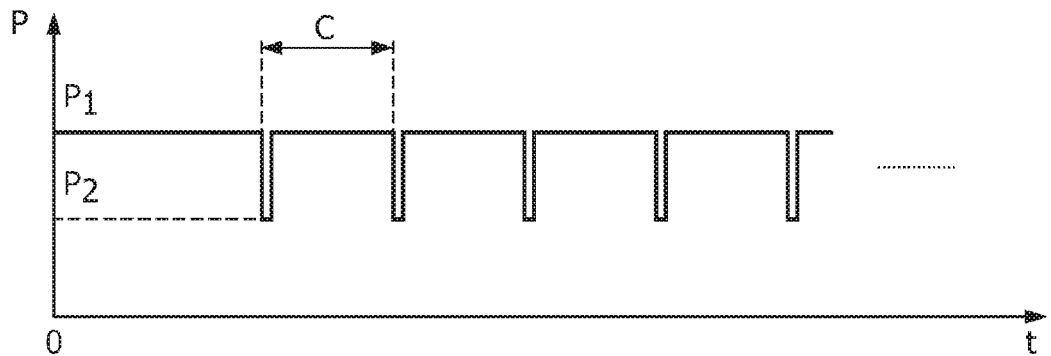
FIG. 2*a* shows one example of heating power curve that may be applied to the food processing device of FIG. 1 to determine core temperature of food.
Figure 2B:
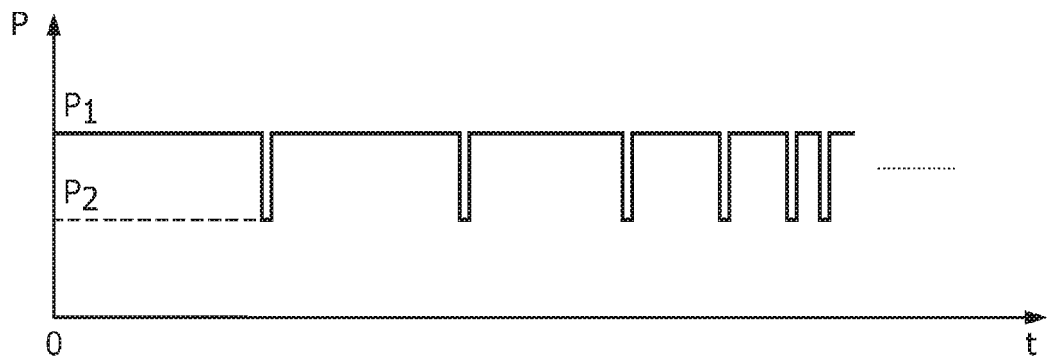
FIG. 2*b* shows another example of heating power curve that may be applied to the food processing device of FIG. 1 to determine core temperature of food.

The number of adjustments of heating power depends on user's requirements for getting known the core temperature of food 101. Typically, a plurality of adjustments of heating power of heater 103 may be performed in such a way that the core temperature of food 101 and thus the doneness of food 101 can be monitored in real time. The plurality of adjustments of heating power of heater 103 may for example be periodic, as shown in FIG. 2a. Alternatively, the adjustments of heating power of heater 103 may be non-periodic, for instance, the frequency of the adjustments may gradually increase with the lapse of cooking time, as shown in FIG. 2b. It is to be noted that the number of adjustments of heating power may also be one to meet different requirements.

The adjustments of heating power of heater 103 can take on various forms. In one example, controller 105 may periodically decrease the heating power of heater 103 from a first level $P_1$ to a second level $P_2$ at the later stage of cooking, as shown in FIG. 2a, and as a result the internal temperature of container 102 drops during each duration where the heating power is at the second level $P_2$. With the lapse of cooking time, the core temperature of food 101 gradually goes up; the higher the core temperature of food 101 is, the lower the drop rate of internal temperature of container 102 will be. Therefore, the drop rate of internal temperature of container 102 can be used to infer the core temperature of food 101.

In another example, controller 105 may periodically increase the heating power of heater 103 from a first level to a second level, and as a result the internal temperature of container 102 rises during each duration where the heating power is at the second level. With the lapse of cooking time, the core temperature of food 101 gradually goes up; the higher the core temperature of food 101 is, the higher the rising rate of internal temperature of container 102 will be.

In this regard, the rising rate of internal temperature of container 102 can also be used to infer the core temperature of food 101.

Hereinafter, the control procedure of controller 105 will be described in details using the periodic decreases of heating power of heater 103 as an example of the adjustments of heating power.

Referring to FIG. 2a, controller 105 decreases the heating power of heating 103 from the first level $P_1$ to the second level $P_2$ periodically at the later stage of cooking. For each cycle C, the duration of second level $P_2$ may be so predetermined that a well compromise between the measurement accuracy and heating time (i.e., power consumption and user convenience) is achieved. During the duration of second level of each cycle (hereinafter, referred to as 'low heating power period'), controller 105 controls sensor 104 to measure a plurality of internal temperature values of container 102. After the measurement, controller 105 receives the plurality of internal temperature values from sensor 104 and calculates the drop rate of internal temperature of container 102 based on the plurality of internal temperature values. The calculation of the drop rate of internal temperature of container 102 will be described later. After that, controller 105 determines the core temperature of food 101 based on the calculated drop rate of internal temperature of container 102 and one set of predetermined relationships between drop rates of internal temperature of a container and core temperatures of food of the same kind/category as food 101. The predetermined relationships may be pre-stored in the storage of controller 105, for example. Alternatively, the predetermined relationships may also be stored in an external storage and controller 105 may acquire them from the external storage while needed. To make food processing device 100 applicable to food of various categories, different sets of predetermined relationships corresponding to different food categories may be pre-stored in the storage of controller 105 or in the external storage, and controller 105 may choose the set of predetermined relationships that corresponds to food 101 when determining the core temperature of food 101.

It is to be noted, in other embodiments, sensor 104 may keep measuring internal temperature values of container 102 periodically during the entire cooking process of food 101. In this case, controller 105 may first screen out those internal temperature values of container 102 corresponding to the low heating power period and then perform the calculation.

The predetermined relationships between drop rates of internal temperature of a container (also referred to as 'sample container' in the following text) and core temperatures of food of the same kind/category as food 101 (also referred to as 'sample food' in the following text) may be obtained, for example, by experiment. One embodiment of the acquisition of the predetermined relationships is described as follows with reference to FIGS. 3a and 3b.

It can be seen from FIG. 3a that during the whole cooking process of the sample food, the heating power of heater of the sample container is controlled to decrease periodically from $P_1$ to $P_2$. In FIG. 3b, $T_a$ curve represents the internal temperature of the sample container and $T(\vec{s}_0)$ curve represents the core temperature of the sample food.

For the first cycle (i.e., between $t=t_0$ to $t=t_0+Z_1+Z_2$), first, a plurality of internal temperature values $T_a$, corresponding to the low heating power period (i.e., between $t=t_0$ to $t=t_0+Z_1$), of the sample container in which the sample food is cooked is obtained.

Second, curve fitting on the obtained plurality of internal temperature values $T_a$ is conducted with a template function. The choice of a fitting template mainly depends on the sample food thermal properties, duration of $Z_1$ and the sample container used. The simplest choice is a linear function if the goodness of fitting satisfies, as shown by the above equation (4), but other functions are also possible, such as a second order polynomial, an exponential function or a logarithmic function. In the case of linear fitting, the drop rate $R_{t_0}$ is given by the resultant slope, i.e., $$R_{t_0} = h(T(t_0, \vec{s}_0)) \tag{5}$$

when referring back to the above equation (4). In the case of a second order polynomial fitting, $R_{t_0}$ is the coefficient of the quadratic term; while for an exponential fitting, $R_{t_0}$ is the coefficient in the exponent.

Third, the relation between the drop rate $R_{t_0}$ and the core temperature of the sample food is experimentally determined. In the case of a linear fitting, $T(t_0, \vec{s}_0)$ can be derived by solving the equation (5). Furthermore, if h( ) is a linear function, i.e., $$h(T(t_0, \vec{s}_0)) = K_1 \times T(\vec{s}_0) + K_0 \tag{6}$$

where $K_1$ and $K_0$ are constants experimentally determined, then the core temperature equals $$T(t_0, \vec{s}_0) = (R_{t_0} - K_0)/K_1 \tag{7}$$

$K_1$ takes a negative sign as the higher core temperature results in a slower internal temperature drop of the sample container.

The above three steps are repeated for the subsequent cycles such that the relationships between drop rates of internal temperature of the sample container and core temperatures of the sample food are derived.

As can be seen from FIG. 3b, the extreme value of decrease of internal temperature of the sample container during low heating power period of each cycle follows the same trend as the core temperature of the sample food; therefore it may also be used to infer the core temperature of sample food as well. In this regard, controller 105 may only need to control sensor 104 to measure the extreme value of decrease of internal temperature of container 102 during low heating power period of each cycle, and then determine the core temperature of food 101 based on the received extreme value of decrease of internal temperature of container 102 and the set of predetermined relationships between extreme values of decrease of internal temperature of a container and core temperature of a food of the same kind/category as food 101. Furthermore, as shown in FIG. 3b, the rising rate of internal temperature of sample container when the heating power is switched back to the first level $P_1$ from the second level $P_2$ also follows the same trend as the core temperature of the sample food, thus it may also be employed.

It shall be appreciated that any feature derivable from the $T_a$ curve that is able to indicate the core temperature of food 101 falls into the scope of the invention.

Advantageously, after determining the core temperature of food 101, controller 105 may further control heater 103 to continue or stop heating food 101 based on the determined core temperature of food 101. If the determined core temperature shows that food 101 is under-cooked, then controller 105 may control heater 103 to continue heating food 101; if the determined core temperature indicates that food 101 has been well cooked, then controller 105 may control heater 103 to stop heating food 101.

Alternatively, food processing device 100 may further comprise a display (not shown). After determining the core temperature of food 101, the display may display the determined core temperature of food 101. With the displayed core temperature of food 101, user may perform subsequent operations, such as, switch off heater 103 if the core temperature of food 101 indicates that food 101 has been well cooked.

It is to be noted that the dynamic heating strategy shown in FIGS. 2a, 2b and 3a are only illustrative. Those skilled in the art can appreciate that the period and duty cycle (for period measurement), pattern (for non periodic measurement), waveform and magnitude of the dynamic heating strategy may be optimized to compromise between the measurement accuracy and heating time (i.e., power consumption and user convenience).

Food processing device 100 may be an oven or other kitchen appliances.

Figure 4:
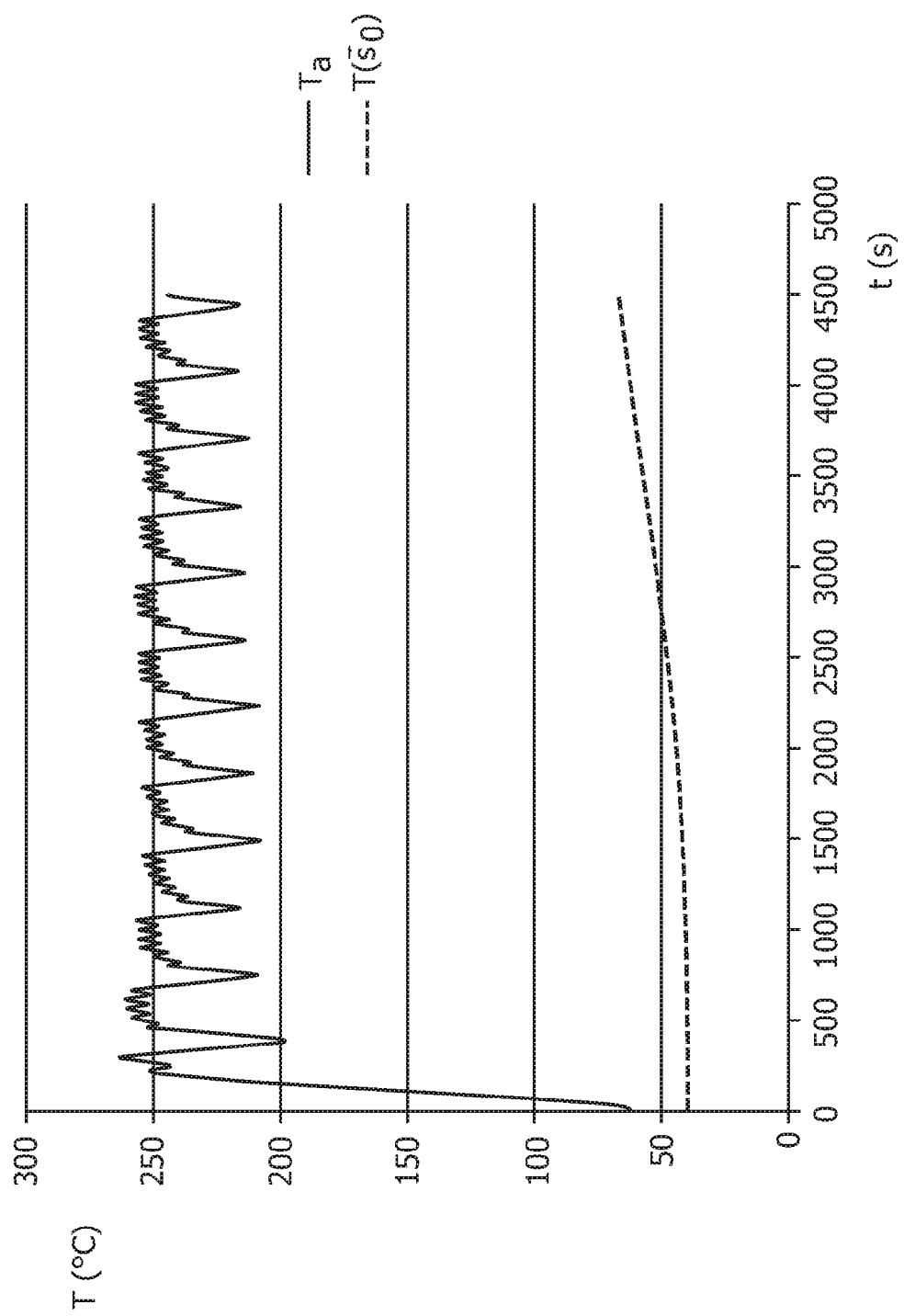
FIG. 4 shows curves of core temperature of a rice cake and internal temperature of a baking oven.
Figure 5:
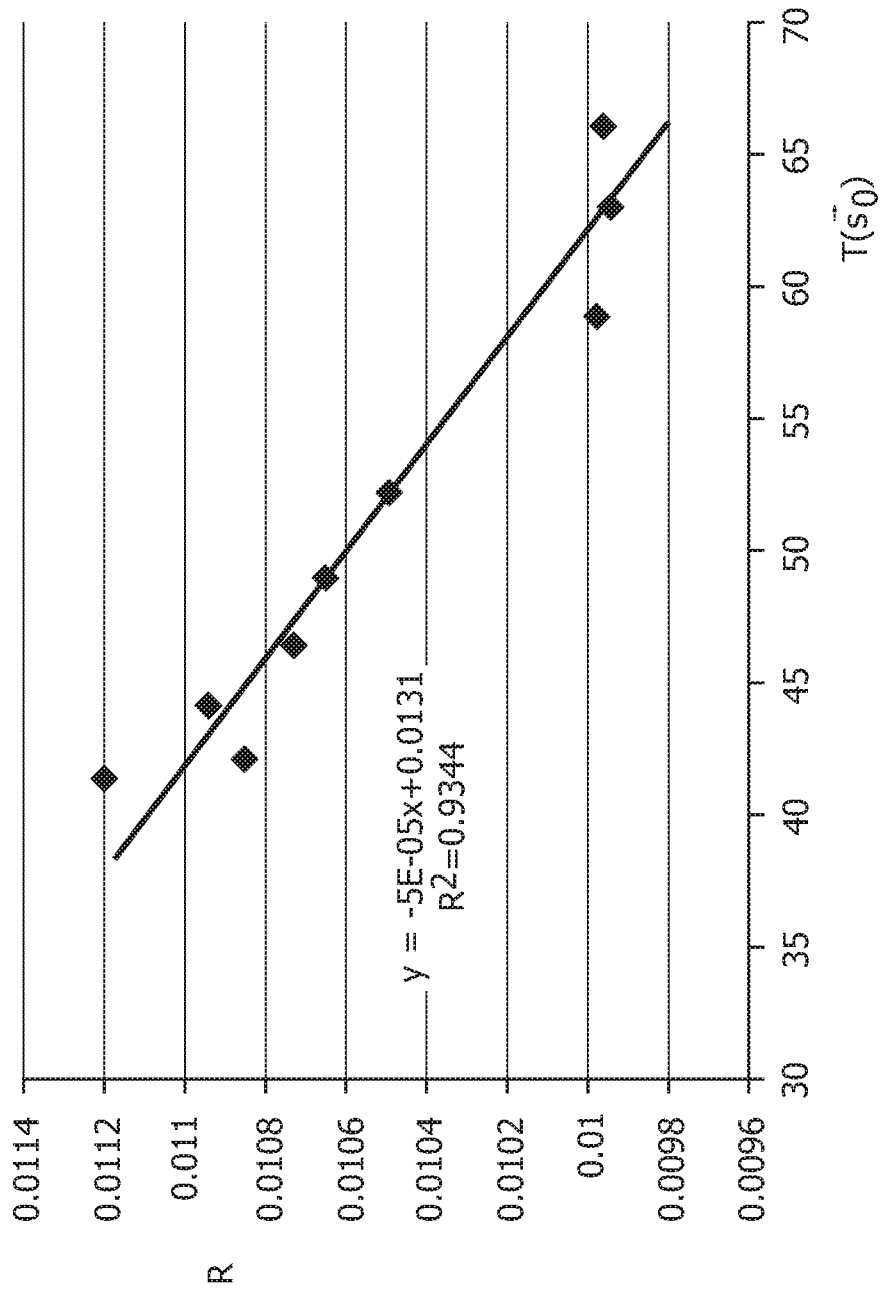
FIG. 5 shows a correlation between the drop rate of internal temperature of a baking oven and the core temperature of a rice cake.

In the following text, a test example is given with reference to FIGS. 4 and 5.

The test was done with a home baking oven. In the test, a rice cake of 14.5×10×7 cm (l×d×h) was heated roughly at the center of the oven. The temperature was set at 250° C. The heating cycle was 6 minutes in which the heating power was switched off for 1 minute. In these 1-minute durations, the drop rate of internal temperature of the oven was recorded and its relation with the core temperature of the rice cake got studied. The thermocouple sensor was used to measure the internal temperature of the oven and the temperature at the geometrical center (i.e., the core temperature) of the rice cake. The measured temperatures are plotted in FIG. 4, where the decaying parts of $T_a$ curve correspond to the switch-off periods of the heating power.

Following the processing steps described above, an exponential function was chosen as the curve fitting template, i.e., $$T_a = K \times e^{-R \times t}$$

to fit the temperature decaying parts of $T_a$ curve, and then got the drop rate of internal temperature of the oven for each cycle. To establish the prediction model, a linear regression was applied to associate the derived drop rates of internal temperature of the oven with the measured core temperatures of the rice cake. The result is shown in FIG. 5. The relation between the drop rate R of internal temperature of the oven and the core temperature $T(\vec{s}_0)$ of the rice cake may be very well described as a linear function of $$T(\vec{s}_0) = 2 \times 10^4 \times (0.0131 - R)$$

with a Pearson's coefficient of 0.9344 that implies a very good fit.

Figure 6:
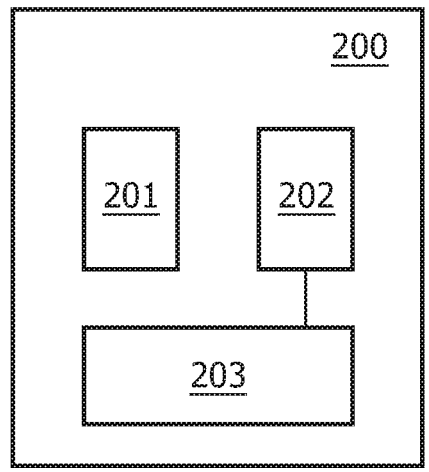
FIG. 6 shows an apparatus for determining core temperature of food according to one embodiment of the invention.

FIG. 6 illustrates an apparatus 200 for determining core temperature of food in a closed container Apparatus 200 comprises an adjusting unit 201, an obtaining unit 202 and a determining unit 203. Apparatus 200 may be incorporated into a food processing device, for example, the food processing device 100 as shown in FIG. 1.

Figure 7:
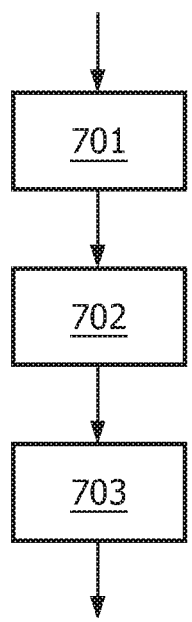
FIG. 7 shows a flow chart of a method of determining core temperature of food according to one embodiment of the invention.

Hereinafter, the operation of apparatus 200 is described in conjunction with FIG. 7. In Step 701, adjusting unit 201 is configured to adjust heating power supplied to the container to allow internal temperature of the container to change within a predetermined duration. Then, in Step 702, obtaining unit 202 is configured to obtain information related to change of internal temperature of the container. Next, in Step 703, determining unit 203 is configured to determine the core temperature of the food based on the information related to the change of internal temperature and predetermined relationships between information related to change of internal temperature of the container and core temperatures of the food.

In one example, the information related to the change of internal temperature comprises a rate of the change of internal temperature, and obtaining unit 202 may comprise a first sensing unit configured to measure a plurality of internal temperature values of the container during the predetermined duration at a predetermined distance away from the food in the container; and a calculating unit configured to calculate the rate of the change of internal temperature of the container based on the plurality of internal temperature values.

In another example, the information related to the change of internal temperature comprises an extreme value of the change of internal temperature, and the obtaining unit may comprise a second sensing unit configured to measure the extreme value of the change of internal temperature of the container during the predetermined duration at a predetermined distance away from the food in the container.

It should be noted that the above described embodiments are given for describing rather than limiting the invention, and it is to be understood that modifications and variations may be resorted to without departing from the spirit and scope of the invention as those skilled in the art readily understand. Such modifications and variations are considered to be within the scope of the invention and the appended claims. The protection scope of the invention is defined by the accompanying claims. In addition, any of the reference numerals in the claims should not be interpreted as a limitation to the claims. Use of the verb "comprise" and its conjugations does not exclude the presence of elements or steps other than those stated in a claim. The indefinite article "a" or "an" preceding an element or step does not exclude the presence of a plurality of such elements or steps.

What is claimed is:

1. A method of determining a core temperature of food in a closed container, the method comprising the steps of:
   adjusting heating power supplied to the closed container between a first power level and a second power level to allow an internal temperature of the closed container to change within a predetermined duration;
   obtaining information related to the change of internal temperature of the closed container within the predetermined duration; and
   determining the core temperature of the food based on (i) the information related to the change of internal temperature and (ii) predetermined relationships between (ii)(a) information related to change of internal temperature of the closed container and (ii)(b) core temperatures of a same kind or category food.

2. The method of claim 1, wherein the information related to the change of internal temperature comprises a rate of the change of internal temperature, and the step of obtaining comprises:
   measuring a plurality of internal temperature values of the closed container during the predetermined duration at a predetermined distance away from the food in the closed container; and
   calculating the rate of the change of internal temperature of the closed container based on the plurality of internal temperature values.

3. The method of claim 1, wherein the information related to the change of internal temperature comprises an extreme value of the change of internal temperature, and the step of obtaining comprises:
   measuring the extreme value of the change of internal temperature of the closed container during the predetermined duration at a predetermined distance away from the food in the closed container.

4. The method of claim 1, wherein the step of adjusting comprises:
  decreasing the heating power supplied to the closed container to allow internal temperature of the closed container to decrease within the predetermined duration.

5. The method of claim 1, further comprising the step of:
  displaying the determined core temperature of the food; or
  controlling the heating power supplied to the closed container to (i) continue heating or (ii) stop heating the food based on the determined core temperature of the food.

6. A food processing device, comprising:
  a closed container, configured to receive food within the closed container;
  a heater coupled with the closed container, configured to heat food received in the closed container;
  a sensor arranged in the closed container at a predetermined distance away from the food received in the closed container, configured to measure internal temperature values of the closed container;
  a controller coupled with the heater and the sensor, configured to perform a set of operations of:
    controlling heating power of the heater between a first power level and a second power level to allow internal an internal temperature of the closed container to change within a predetermined duration;
    obtaining information related to the change of internal temperature of the closed container within the predetermined duration based on at least one internal temperature value that is measured by the sensor during the predetermined duration; and
    determining the core temperature of the food based on (i) the information related to the change of internal temperature and (ii) predetermined relationships between (ii)(a) information related to change of internal temperature of the closed container and (ii)(b) core temperatures of a same kind or category of food.

7. The food processing device of claim 6, wherein the information related to the change of internal temperature comprises a rate of the change of internal temperature, wherein the sensor is configured to measure a plurality of internal temperature values of the closed container during the predetermined duration, and wherein the controller is configured to receive the plurality of internal temperature values from the sensor and calculate the rate of the change of internal temperature of the closed container based on the plurality of internal temperature values.

8. The food processing device of claim 6, wherein the information related to the change of internal temperature comprises an extreme value of the change of internal temperature, wherein the sensor is configured to measure the extreme value of the change of internal temperature during the predetermined duration, and wherein the controller is configured to receive the extreme value of the change of internal temperature from the sensor.

9. The food processing device of claim 6, wherein the controller is configured to adjust heating power of the heater to allow internal temperature of the closed container to change within the predetermined duration.

10. The food processing device of claim 6, wherein the controller performs the operations after the food received in the closed container has been cooked for a first predetermined duration.

11. The food processing device of claim 6, wherein the controller performs the set of operations periodically.

12. The food processing device of claim 6, wherein a frequency of performing the set of operations by the controller increases at a later stage of cooking compared to an earlier stage of cooking.

13. An apparatus for determining core temperature of food in a closed container, the apparatus comprising:
  an adjusting unit configured to adjust heating power supplied to the closed container between a first power level and a second power level to allow an internal temperature of the closed container to change within a predetermined duration;
  an obtaining unit configured to obtain information related to change of internal temperature of the closed container within the predetermined duration; and
  a determining unit configured to determine the core temperature of the food based on (i) the information related to the change of internal temperature and (ii) predetermined relationships between (ii)(a) information related to change of internal temperature of the closed container and (i)(b) core temperatures of a same category of food.

14. The apparatus of claim 13, wherein the information related to the change of internal temperature comprises a rate of the change of internal temperature, and the obtaining unit comprises:
  a first sensing unit configured to measure a plurality of internal temperature values of the closed container during the predetermined duration at a predetermined distance away from the food in the closed container;
  a calculating unit configured to calculate the rate of the change of internal temperature of the closed container based on the plurality of internal temperature values.

15. The apparatus of claim 13, wherein the information related to the change of internal temperature comprises an extreme value of the change of internal temperature, and the obtaining unit comprises:
  a second sensing unit configured to measure the extreme value of the change of internal temperature of the closed container during the predetermined duration at a predetermined distance away from the food in the closed container.

* * * * *